(12) United States Patent
Carter

(10) Patent No.: US 7,771,391 B2
(45) Date of Patent: Aug. 10, 2010

(54) DISPOSABLE INFUSION DEVICE WITH SNAP ACTION ACTUATION

(75) Inventor: Brett J. Carter, Monroe, WA (US)

(73) Assignee: Calibra Medical, Inc., Redwood City ( * ) Notice: Subject to any disclaimer, the term of this patent is extended or adjusted under 35 U.S.C. 154(b) by 129 days.

(21) Appl. No.: 11/906,102

(22) Filed: Sep. 28, 2007

(65) Prior Publication Data

US 2009/0088689 A1   Apr. 2, 2009

(51) Int. Cl.
*A61M 1/00* (2006.01)
(52) U.S. Cl. ................................. 604/151; 604/180
(58) Field of Classification Search ........... 604/125, 604/131, 132, 134, 136, 151
See application file for complete search history.

(56) References Cited

U.S. PATENT DOCUMENTS

| | | | |
|---|---|---|---|
| 5,997,501 A * | 12/1999 | Gross et al. ................ 604/65 |
| 6,186,982 B1 * | 2/2001 | Gross et al. ................ 604/132 |
| 6,500,150 B1 * | 12/2002 | Gross et al. ................ 604/131 |
| 6,679,862 B2 * | 1/2004 | Diaz et al. ................. 604/151 |
| 6,702,779 B2 | 3/2004 | Connelly et al. |
| 6,824,529 B2 | 11/2004 | Gross et al. |
| 6,923,791 B2 | 8/2005 | Douglas |
| 7,128,727 B2 * | 10/2006 | Flaherty et al. ............ 604/131 |
| 2001/0025168 A1 * | 9/2001 | Gross et al. ................ 604/506 |
| 2004/0064096 A1 * | 4/2004 | Flaherty et al. ............ 604/131 |
| 2004/0116865 A1 * | 6/2004 | Bengtsson .................. 604/171 |
| 2004/0138612 A1 * | 7/2004 | Shermer et al. ........... 604/93.01 |
| 2004/0260235 A1 * | 12/2004 | Douglas ................... 604/93.01 |
| 2005/0107743 A1 | 5/2005 | Fangrow, Jr. |
| 2008/0097318 A1 * | 4/2008 | Adams ...................... 604/131 |
| 2008/0119790 A1 * | 5/2008 | Hawkins et al. ........... 604/131 |

OTHER PUBLICATIONS

International Search Report for PCT/US2008-077320, dated Sep. 23, 2008, conducted by Korean Intellectual Property Office, Republic of Korea.

* cited by examiner

*Primary Examiner*—Nicholas D Lucchesi
*Assistant Examiner*—Gerald Landry, II
(74) *Attorney, Agent, or Firm*—Richard O. Gray, Jr.; Graybeal Jackson LLP

(57) ABSTRACT

A wearable infusion device comprises a reservoir that holds a liquid medicament, an outlet port that delivers the liquid medicament to a patient, a pump that displaces a volume of the liquid medicament to the outlet port when actuated, and a control that actuates the pump. The control comprises a snap action actuator.

11 Claims, 11 Drawing Sheets

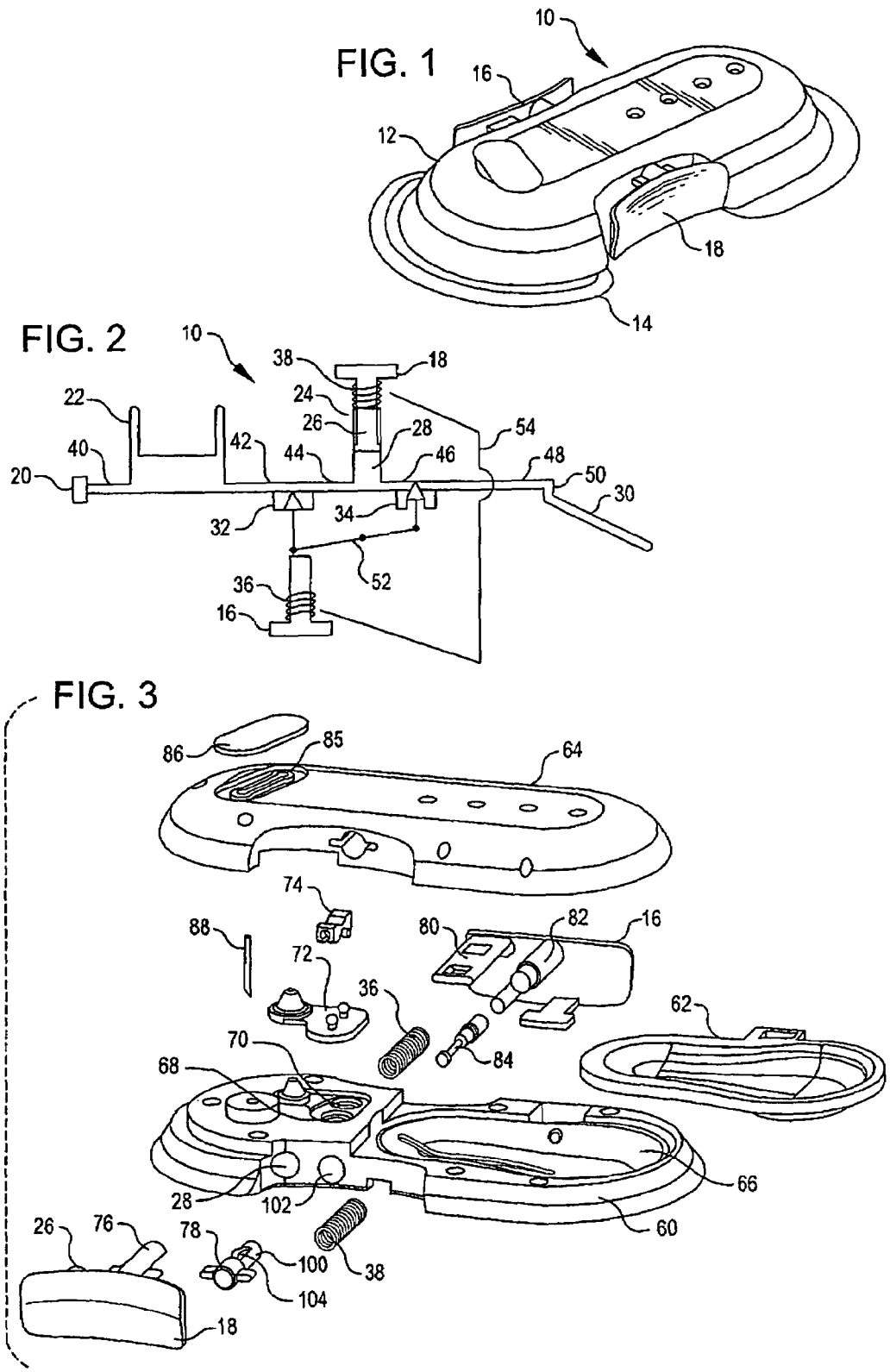

DISPOSABLE INFUSION DEVICE WITH SNAP ACTION ACTUATION

BACKGROUND OF THE INVENTION

The present invention relates to infusion devices and more particularly to such devices that enable liquid medicaments to be conveniently and safely self-administered by a patient.

Tight control over the delivery of insulin in both type I diabetes (usually juvenile onset) and type II diabetes (usually late adult onset), has been shown to improve the quality of life as well as the general health of these patients. Insulin delivery has been dominated by subcutaneous injections of both long acting insulin to cover the basal needs of the patient and by short acting insulin to compensate for meals and snacks. Recently, the development of electronic, external insulin infusion pumps has allowed the continuous infusion of fast acting insulin for the maintenance of the basal needs as well as the compensatory doses (boluses) for meals and snacks. These infusion systems have shown to improve control of blood glucose levels. However, they suffer the drawbacks of size, cost, and complexity. For example, these pumps are electronically controlled and must be programmed to supply the desired amounts of basal and bolus insulin. This prevents many patients from accepting this technology over the standard subcutaneous injections.

Hence, there is a need in the art for a convenient form of insulin treatment which does not require significant programming or technical skills to implement to service both basal and bolus needs. Preferably, such a treatment would be carried out by an infusion device that is simple to use and mechanically driven negating the need for batteries and the like. It would also be preferable if the infusion device could be directly attached to the body and not require any electronics to program the delivery rates. The insulin is preferably delivered through a small, thin-walled tubing (cannula) through the skin into the subcutaneous tissue similar to technologies in the prior art.

While the idea of such a simple insulin delivery device is compelling, many obstacles must be overcome before such a device may become a practical realty. One problem resides in insulin supply. Patients vary greatly on the amount of insulin such a device must carry to provide treatment over a fixed time period of, for example, three days. This is one environment where one size does not fit all. Still further, such devices must be wearable with safety and not subject to possible accidental dosing. Still further, such devices must be capable of delivering an accurately controlled volume of medicament with reliability. While it is preferred that these devices include all of the forgoing features, it would be further preferred if the cost of manufacturing such a device would be economical enough so as to render the device disposable after use. As will be seen subsequently, the devices and methods described herein address these and other issues.

SUMMARY OF THE INVENTION

In one embodiment, the invention provides a wearable infusion device comprising a reservoir that holds a liquid medicament, an outlet port that delivers the liquid medicament to a patient, a pump that displaces a volume of the liquid medicament to the outlet port when actuated, and a control comprising a snap action actuator that actuates the pump.

The snap action actuator may comprise a depressible member or a bendable member. The snap action actuator may further comprise an abutment member that initially engages and holds the bendable member under compression. The snap action actuator may further comprise a first cam surface that, when translated in a first direction, raises the bendable member above the abutment member to release the bendable member. The snap action actuator may further comprise a second cam surface that, when translated in a second direction, opposite the first direction, raises the bendable member above the abutment member and returns the bendable member into engagement with the abutment member under compression. The device may further comprise a spring that forces the second cam surface to translate in the second direction.

The snap action actuator may further comprise a first cam surface that, when translated in a direction towards the bendable member, raises the bendable member above the abutment member to release the bendable member. The snap action actuator may further comprise a second cam surface that, when translated in a direction away from the bendable member, raises the bendable member above the abutment member and returns the bendable member into engagement with the abutment member under compression. The device may further comprise a spring that forces the second cam surface to translate in the direction away from the bendable member.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

FIG. 1 is a perspective view of a first infusion device embodying certain aspects of the present invention;

FIG. 2 is a schematic representation of the valves and pump of the device of FIG. 1;

FIG. 3 is an exploded perspective view of the device of FIG. 1;

DETAILED DESCRIPTION OF THE INVENTION

Figure 4:
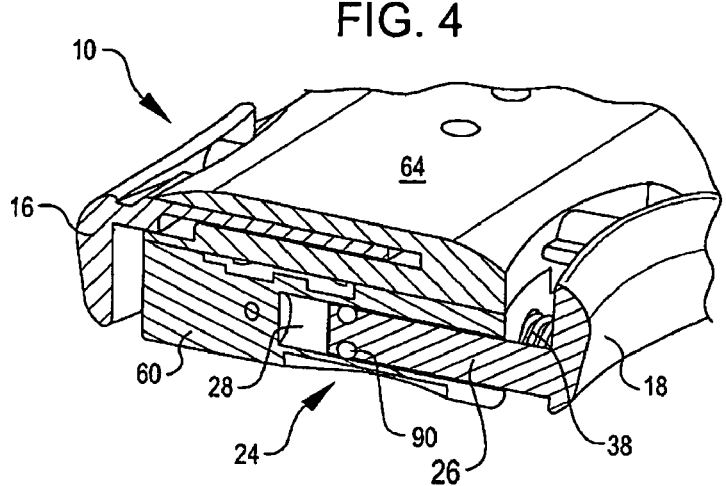
FIG. 4 is a sectional view, in perspective, of the device of FIG. 1 showing the pump of the device directly coupled to an actuator button.

Referring now to FIG. 1 it is a perspective view of a first infusion device embodying certain aspects of the present invention. The device 10 generally includes an enclosure 12, a base 14, a first actuator control button 16, and a second actuator control button 18.

The enclosure 12, as will be seen subsequently, is formed by virtue of multiple device layers being brought together. Each layer defines various components of the device such as, for example, a reservoir, fluid conduits, pump chambers, and valve chambers, for example. This form of device construction, in accordance with aspects of the present invention, enables manufacturing economy to an extent rendering the device disposable after use.

The base 14 preferably includes an adhesive coating to permit the device to be adhered to a patient's skin. The adhesive coating may originally be covered with a releasable cover that may be peeled off of the base 14 when the patient endeavors to deploy the device 10. Such arrangements are well known in the art.

The device 10 may be mated with a previously deployed cannula assembly. However, it is contemplated herein that the various aspects of the present invention may be realized within a device that may be alternatively first adhered to the patient's skin followed by the deployment of a cannula thereafter.

The actuator buttons 16 and 18 are placed on opposites sides of the device 10 and directly across from each other. This renders more convenient the concurrent depression of the buttons when the patient wishes to receive a dose of the liquid medicament contained within the device 10. This arrangement also imposes substantially equal and opposite forces on the device during dosage delivery to prevent the device from being displaced and possibly stripped from the patient. As will be further seen hereinafter, the concurrent depression of the buttons is used to particular advantage. More specifically, the actuator button 16 may serve as a valve control which, when in a first position as shown, establishes a first fluid path between the device reservoir and the device pump to support pump filling, and then, when in a second or depressed position, establishes a second fluid path between the device pump and the device outlet or cannula to permit dosage delivery to the patient. As will be further seen, a linkage between the control actuator buttons 16 and 18 permits actuation of the device pump with the actuator control button 18 only when the second fluid path has been established by the first actuator control button 16. Hence, the first actuator control button 16 may be considered a safety control.

Referring now to FIG. 2, it is a schematic representation of the valves and pump of the device 10 of FIG. 1. As may be seen in FIG. 2, the device 10 further includes a fill port 20, a reservoir 22, a pump 24, and the cannula 30. The device further includes a first valve 32 and a second valve 34. Fluid conduit 40 provides a fluid connection between the fill port 20 and the reservoir 22, fluid conduit 42 provides a fluid connection between the reservoir 22 and the first valve 32, fluid conduit 44 provides a fluid connection between the first valve 32 and the pump 24, fluid conduit 46 provides a fluid connection between the pump 24 and the second valve 34, and fluid conduit 48 provides a fluid connection between the second valve 34 and the device outlet 50. The outlet 50 is arranged to communicate with the cannula 30.

It may also be noted that the actuator buttons 16 and 18 are spring loaded by springs 36 and 38. The springs are provided for returning the actuator buttons to the first position after a dosage is administered.

The pump 24 of the device 10 comprises a piston pump. The pump 24 includes a pump piston 26 and a pump chamber 28. In accordance with this embodiment, the actuator control button 18 is directly coupled to and is an extension of the pump piston 26.

With further reference to FIG. 2, the device additionally includes a first linkage 52 and a second linkage 54. The first linkage is a toggle linkage between the first valve 32 and the second valve 34. It is arranged to assure that the second valve 34 does not open until after the first valve 32 is closed. The second linkage 54 is between the first actuator button 16 and the second actuator button 18. It is arranged to assure that the pump does not pump until after the first valve is closed and the second valve is opened by the first actuator button 16.

Still further, the second valve 34 is a safety valve that closes tighter responsive to increased fluid pressure within fluid conduit 46. This assures that the liquid medicament is not accidentally administered to the patient notwithstanding the inadvertent application of pressure to the reservoir, for example. In applications such as this, it is not uncommon for the reservoir to be formed of flexible material. While this has its advantages, it does present the risk that the reservoir may be accidentally squeezed as it is worn. Because the second valve only closes tighter under such conditions, it is assured that increased accidental reservoir pressure will not cause the fluid medicament to flow to the cannula.

In operation, the reservoir is first filled through the fill port 20 to a desired level of medicament. In this state, the valves 32 and 34 will be as shown. The first valve 32 will be open and the second valve 34 will be closed. This permits the piston chamber 28 to be filled after the reservoir is filled. The cannula 30 may then be deployed followed by the deployment of the device 10. In this state, the valves 32 and 34 will still be as shown. The first valve 32 will be open and the second valve 34 will be closed. This permits the pump chamber 28 to be filled through a first fluid path including conduits 42 and 44 as the piston 24 returns to its first position after each applied dose.

When the patient wishes to receive a dose of medicament, the actuator buttons are concurrently pressed. In accordance with aspects of the present invention, the linkage 52 causes the first valve 32 to close and the second valve 34 to thereafter open. Meanwhile, the second linkage 54 precludes actuation of the pump 24 until the first valve 32 is closed and the second valve 34 is opened by the first actuator button 16. At this point a second fluid path is established from the pump 24 to the cannula 30 through fluid conduits 46 and 48 and the outlet 50. The medicament is then administered to the patient through cannula 30.

Once the medication dosage is administered, the piston 24, and thus the actuator button 18, is returned under the spring pressure of spring 38 to its initial position. During the travel of the piston back to its first position, a given volume of the liquid medicament for the next dosage delivery is drawn from the reservoir into the pump chamber 28 to ready the device for its next dosage delivery.

Referring now to FIG. 3, it is an exploded perspective view of the device of FIG. 1. It shows the various component parts of the device. The main component parts include the aforementioned device layers including the base layer 60, the reservoir membrane or intermediate layer 62, and the top body layer 64. The base layer is a substantially rigid unitary structure that defines a first reservoir portion 66, the pump chamber 28, and valve sockets 68 and 70 of the first and second valves respectively. The base layer 60 may be formed of plastic, for example. The reservoir membrane layer 62 is received over the reservoir portion 66 to form the reservoir 22 (FIG. 2). A valve seat structure 72 is received over the valve sockets 68 and 70 to form the first and second valves 32 and 34 (FIG. 2) respectively. A rocker 74 is placed over the valves seat structure 72 to open and close the valves as will be seen subsequently. The pump actuator button 18 carries the pump piston that is received within the pump chamber 28. The pump actuator button 18 also carries a cam cylinder 76 with a lock tube 78 therein that form a portion of the second linkage 54 (FIG. 2). The spring 38 returns the actuator button 18 to its first position after each dosage delivery.

The first actuator control button carries a valve timing cam 80 that rocks the rocker 72. The button 16 further carries a cam cylinder 82 and a cam pin 84 that is received into the cam cylinder 82. The spring 36 returns the actuator button 16 to its first position after each dosage delivery. The top body layer 64 forms the top portion of the device enclosure. It receives a planar cap 86 that completes fluid paths 85 partially formed in the top layer 64. Lastly, a needle 88 is provided that provides fluid coupling from the cannula (not shown) to the outlet of the device 10.

FIG. 4 shows a sectional view, in perspective, of the device of FIG. 1. More specifically, the figure shows details of the piston pump 24 within the device 10. Here, it may be seen that the piston 26 of the piston pump 24 is received within the pump chamber 28 that is formed in the base layer 60 of the device. The piston 26 may further be seen to be an extension of the actuator button 18. An O-ring 90 provides a seal between the pump chamber 28 and the piston 26. The spring 38 returns the actuator button 18 to its shown first position after each dosage delivery.

Figure 5:
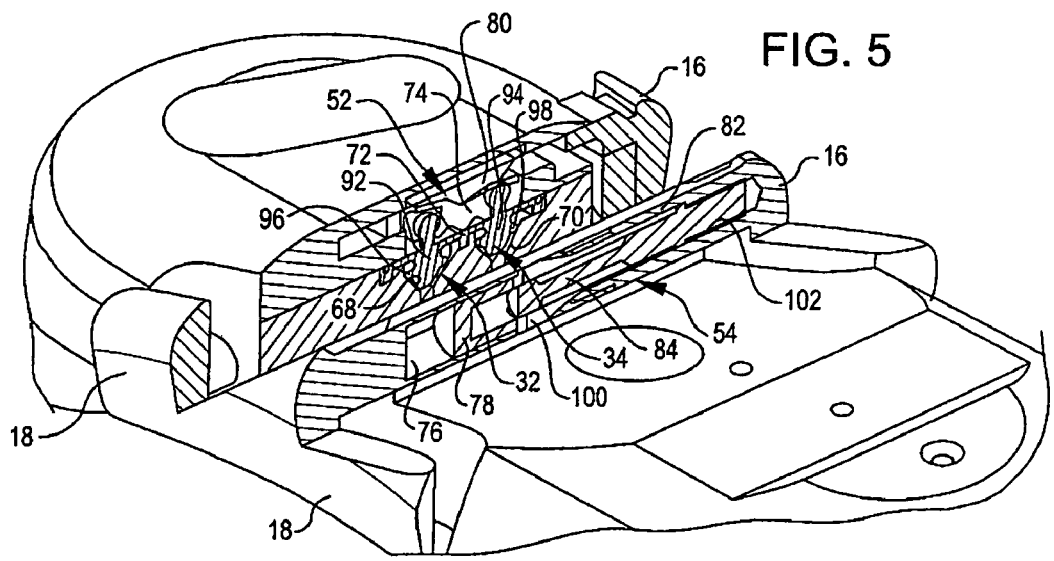
FIG. 5 is a sectional view, in perspective, of the device of FIG. 1 showing the valves and the valve and actuation linkages prior to the delivery of a medicament dose.

FIG. 5 is a sectional view, in perspective, of the device of FIG. 1 showing the valves 32 and 34 and the valve and actuation linkages prior to the delivery of a medicament dose. The valves will first be described. First, it may be noted that the valve seat structure 72 is received within the valve sockets 68 and 70. The valve seat structure 72 includes valve seats 92 and 94 that are received within the valve sockets 68 and 70 respectively. Each of the seats 92 and 94 has a widened portion 96 and 98, respectively, that cause the seats to be more tightly seated within sockets 68 and 70 in response to increased fluid pressure in the downward direction. As previously described, this protects against the potential effects of accidental medication delivery due to external pressure being applied to the reservoir of the device.

The rocker 74 opens and closes the valves 32 and 34. It is under control of the timing cam 80 carried by the first actuator control button 16. As the control button 16 is moved laterally, the cam 80 causes the rocker 74 to pivot and to apply pressure to one or the other of the valve seats 92 or 94. The shape of the cam surfaces on the rocker 74 and the cam 80 assure that the valve 34 will not open until the valve 32 closes. The cam 80 and rocker 74 thus form the first linkage 52 shown in FIG. 2.

While the cam 80 and rocker 74 are operating the valves 32 and 34 under timing control provided by the first linkage 52, the second linkage 54 is controlling when the pump may displace liquid medicament form the pump chamber 28 to the device outlet and cannula. FIGS. 5-8 show details of the second linkage.

Figure 6:
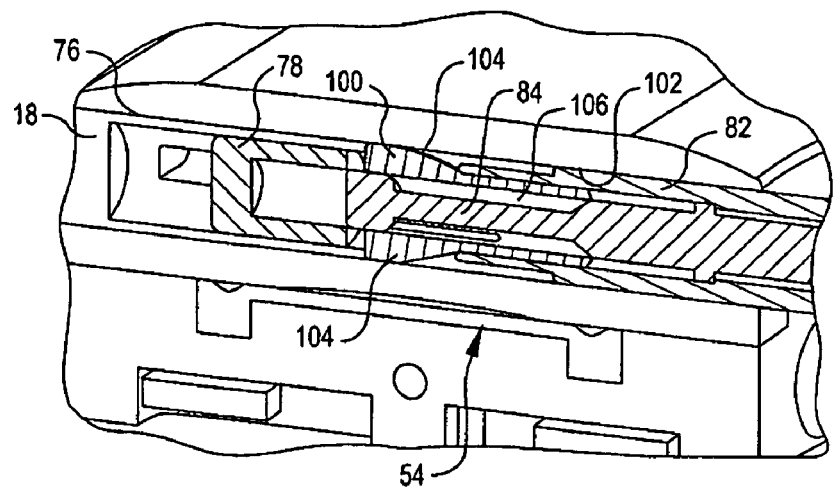
FIG. 6 is a sectional view, to an enlarged scale, illustrating the actuation linkages prior to the delivery of a medicament dose.

As may be seen in FIGS. 5 and 6, the second linkage includes the cam cylinder 76, the lock tube 78, the outer cam cylinder 82, and the cam pin 84. The cam cylinder is integral with the second actuator control button 18 and the outer cam cylinder 82 is integral with the first actuator control button. The second linkage 54 further includes a lock cylinder 100. The foregoing are disposed in a bore 102 formed in the base layer 60 of the device.

When the actuator buttons are in their first position as shown in FIG. 6, the end of the lock tube 78 abuts the end of the lock cylinder 100. The lock cylinder includes ears 104. When a dosage delivery is desired, the concurrent pushing of the buttons 16 and 18 causes the outer cam cylinder 82 to slide over the lock cylinder 100 first and then the cam cylinder 76 to slide over the lock tube 78. The sliding of the outer cam cylinder 82 over the lock cylinder 100 causes the first valve to close and the second valve to open. When this is accomplished, the cam cylinder 76 is then permitted to slide over lock tube 78 to cause the piston 26 to move through the pump chamber 28. This displaces the liquid medicament in the pump chamber 28 for delivering the medicament to the cannula 30 and the patient.

Figure 7:
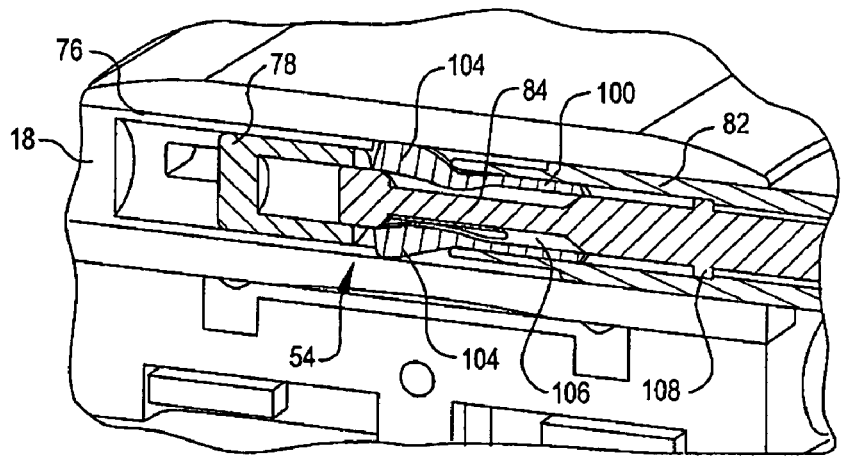
FIG. 7 is a sectional view, like that of FIG. 6, illustrating the actuation linkages during the delivery of a medicament dose.

FIG. 7 illustrates the manner in which the outer cam cylinder 82 slides along the lock cylinder 100. It may first be noted that the cam pin 84 has a reduced diameter portion creating an annular space 106 between the pin 84 and the lock cylinder 100. The outer cam cylinder 82 engages the pin at a flange 108 of the pin 84. This engagement will cause the pin 84 to move with the outer cam cylinder 82. The pushing of the first actuator button 16 will cause the outer cam cylinder 82 to engage the ears 104 of the lock cylinder 100 while at the same time, the end of the pin 84 moves into the lock tube 78. Eventually, the ears 104 are depressed enough by the outer cam cylinder 82 as the end of the pin 84 clears the end of the depressed lock cylinder 100 to permit the ears 104 to enter space 106. This occurs with a snap sound and feel as it occurs suddenly. The outer cam cylinder 82 is now free to slide its complete travel distance over the lock cylinder 100. The valve 32 has now been closed and the valve 34 has been opened.

The snap action of the actuator buttons 16 and 18 provides positive assurance to the patient that a dosage of medicament was delivered. Also, because the snap action only occurs when the pump actuator button 18 completes it full travel, the patient will also know that a full dosage was delivered.

Figure 8:
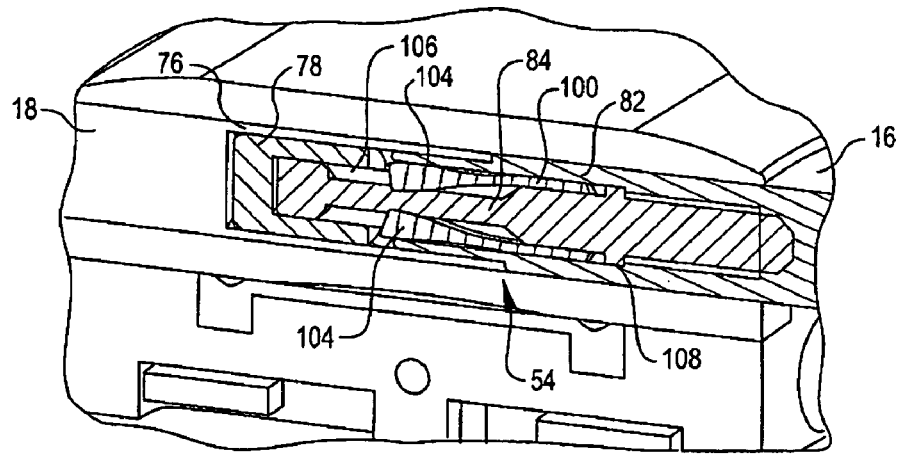
FIG. 8 is a another sectional view, like that of FIG. 5, illustrating the actuation linkages just after the delivery of a medicament dose.

After the outer cam cylinder 82 has completed its travel over the lock cylinder 100, the ears 104 will be displaced sufficiently into space 106 to permit the cam cylinder 76 to clear the end of the lock cylinder 100 and slide over the lock tube 78. The condition of the second linkage 54 at this time is shown in FIG. 8. As previously described, as the cam cylinder 76 slides over the lock tube 78, the pump 24 is actuated to deliver the medicament to the patient.

Figure 9:
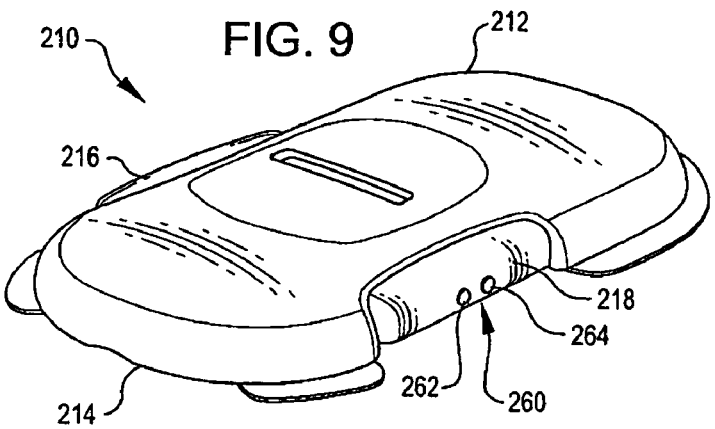
FIG. 9 is a perspective view of another infusion device embodying various aspects of the present invention.

Referring now to FIG. 9, it is a perspective view of another infusion device embodying various aspects of the present invention. The device 210 generally includes an enclosure 212, a base 214, a first actuator control button 216, and a second actuator control button 218.

The enclosure 212 is formed by virtue of multiple device layers being brought together. Each layer defines various components of the device such as, for example, a reservoir, fluid conduits, pumps, and valve chambers, for example. This form of device construction, in accordance with aspects of the present invention, enables manufacturing economy to an extent rendering the device disposable after use.

The base 214 preferably includes an adhesive coating to permit the device to be adhered to a patient's skin. The adhesive coating may originally be covered with a releasable cover that may be pealed off of the base 214 when the patient endeavors to deploy the device 210. Such arrangements are well known in the art.

As will also be seen subsequently, the device 210 may be mated with a previously deployed cannula assembly. However, it is contemplated herein that the various aspects of the present invention may be realized within a device that may be alternatively first adhered to the patient's skin followed by the deployment of a cannula thereafter.

As in the previous embodiment, the actuator buttons 216 and 218 are placed on opposites sides of the device 210 and directly across from each other. This again renders more convenient the concurrent depression of the buttons when the patient wishes to receive a dose of the liquid medicament contained within the device 210. This arrangement also imposes substantially equal and opposite forces on the device during dosage delivery to prevent the device from being displaced and possibly stripped from the patient. As will be further seen hereinafter, the concurrent depression of the buttons is used to particular advantage. More specifically, the actuator button 216 may serve as a valve control which, when in a first position as shown, establishes a first fluid path between the device reservoir and the device pump to support pump filling, and then, when in a second or depressed position, establishes a second fluid path between the device pump and the device outlet or cannula to permit dosage delivery to the patient. As will be further seen, a linkage between the control actuator buttons 216 and 218 permits actuation of the device pump with the actuator control button 218 only when the second fluid path has been established by the first actuator control button 216. Hence, the first actuator control button 216 may be considered a safety control.

With continued reference to FIG. 9, it may be further noted that the device 210 also includes a tactile indicator 260 that represents the volume of the liquid medicament delivered by the device with each actuation of the pump 224. The tactile indicator is carried by the pump actuator button 218 and takes the form of a plurality of distinct raised features or bumps 262 and 264. Alternatively, the tactile indicator may take the form of one or more distinct relieved portions. Each bump 262 and 264 may correspond to a single unit of medicament. Hence, in this embodiment, the bumps 262 and 264 indicate that the device delivers two units of medicament with each actuation of the pump.

Figure 10:
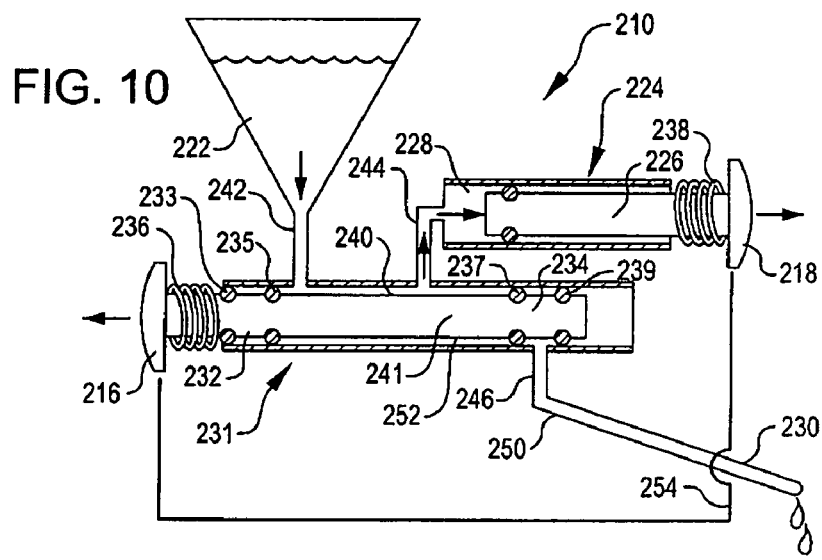
FIG. 10 is a schematic representation of the valves and pump of the device of FIG. 9 between medicament dosage delivery and for filling the pump with the medicament.

The tactile indicator 260 being carried on the pump actuator control button 218 provides a very significant feature and advantage. As will be seen subsequently, the pump actuator button 218 has an integral extension that forms the piston 226 of the piston pump 224 as represented in FIG. 10 to be described hereinafter. It will also be seen that the piston chamber 228 is formed in a component of the device that may be used in devices delivering dosage amounts other than two units. The component may be common to all such devices because it would have a fixed piston chamber length and the dosage amount is determined by the throw of the pump piston 226. Each piston throw is integral to the part and corresponds to a respective given dosage amount. Each pump actuator button for a given dosage amount may have then be provided with a corresponding tactile indicator. Hence, if a tactile indicator indicates a dosage amount of two units, for example, it is assured that that is the medicament amount delivered with that particular pump button. Further, this arrangement is advantageous from a manufacturing standpoint because the actuator buttons for the various dosage size devices cannot be confused with each other.

Figure 11:
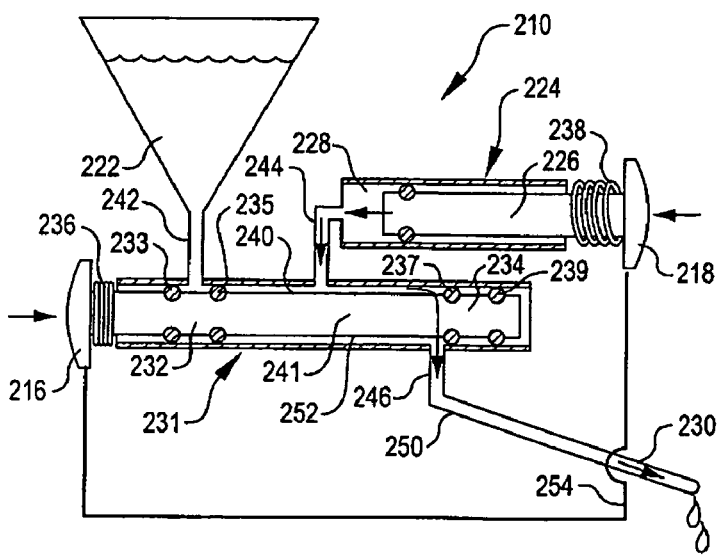
FIG. 11 is a schematic representation of the valves and pump of the device of FIG. 9 during medicament dosage delivery.

Referring now to FIGS. 10 and 11, they are schematic representations of the valves and pump of the device of FIG. 9 between medicament dosage filling (FIG. 10) and medicament dosage delivery (FIG. 11) As may be seen in FIGS. 10 and 11, the device 210 further includes a reservoir 222, a pump 224, and the cannula 230. The device further includes a shuttle valve 231 forming a first valve 232 defined by O-rings 233 and 235 and a second valve 234 defined by O-rings 237 and 239. Although O-rings are used herein to form seals, other types of valve construction may best employ other forms of seals other than O-rings without departing from the invention. Fluid conduit 240 extends between the valves 232 and 234. A fluid conduit 242 provides a fluid connection between the reservoir 222 and the shuttle valve 231 and fluid conduit 244 provides a fluid connection between the shuttle valve 231 and the pump 224. A further fluid conduit 246 provides a fluid connection between the shuttle valve 231 and the device outlet 250. The outlet 250, in the form of a needle, is arranged to communicate with the cannula 230.

It may also be noted that the actuator buttons 216 and 218 are spring loaded by springs 236 and 238. The springs are provided for returning the actuator buttons to the first position after a dosage is administered.

The pump 224 of the device 210 comprises a piston pump. The pump 224 includes a pump piston 226 and a pump chamber 228. In accordance with this embodiment, the actuator control button 218 is directly coupled to and is an extension of the pump piston 226.

With further reference to FIGS. 10 and 11, the device additionally includes a first linkage 252 and a second linkage 254. The first linkage is formed by the shuttle bar 241 of the first valve 232 and the second valve 234. It is arranged by separating the valves 232 and 234 be a distance that assures that the second valve 234 does not open until after the first valve 232 is closed. The second linkage 254 is between the first actuator button 216 and the second actuator button 218. It is arranged to assure that the pump 224 does not pump until after the first valve 232 is closed and the second valve 234 is opened by the first actuator button 216.

Still further, the second valve 234 is a safety valve that assures that the liquid medicament is not accidentally administered to the patient notwithstanding the inadvertent application of pressure to the reservoir, for example. In applications such as this, it is not uncommon for the reservoir to be formed of flexible material. While this has its advantages, it does present the risk that the reservoir may be accidentally squeezed as it is worn. Because of the second valve 234, it is assured that accidental reservoir pressure will not cause the fluid medicament to flow to the cannula.

In operation, the pump chamber 228 is first filled as the actuator button 218 returns to the first position after having just delivered a medicament dosage. In this state, the shuttle valve 231 is set so that the first valve 232 will be open (the reservoir 222 communicates with the fluid conduit 240) and the second valve 234 will be closed (the conduit 246 is closed off from fluid conduit 240). This establishes a first fluid path from the reservoir 222 to the pump 224 through conduits 242, 240 and 244 that permits the piston chamber 228 to be filled by the reservoir as the actuator button is returned to its first position under the influence of the spring 238.

When the patient wishes to receive another dose of medicament, the actuator buttons are concurrently pressed. In accordance with aspects of the present invention, the linkage 252 causes the first valve 232 to close and the second valve 234 to thereafter open. Meanwhile, the second linkage 254 precludes actuation of the pump 224 until the first valve 332 is closed and the second valve 334 is opened by the first actuator button 216. At this point a second fluid path is established from the pump 224 to the cannula 30 through fluid conduits 244, 240 and 246 and the outlet 250. The medicament is then administered to the patient through cannula 30.

Once the medication dosage is administered, the piston 224, and thus the actuator button 218, is returned under the spring pressure of spring 238 to its initial position. During the travel of the piston back to its first position, a given volume of the liquid medicament for the next dosage delivery is drawn from the reservoir into the pump chamber 228 as described above to ready the device for its next dosage delivery.

Figure 12:
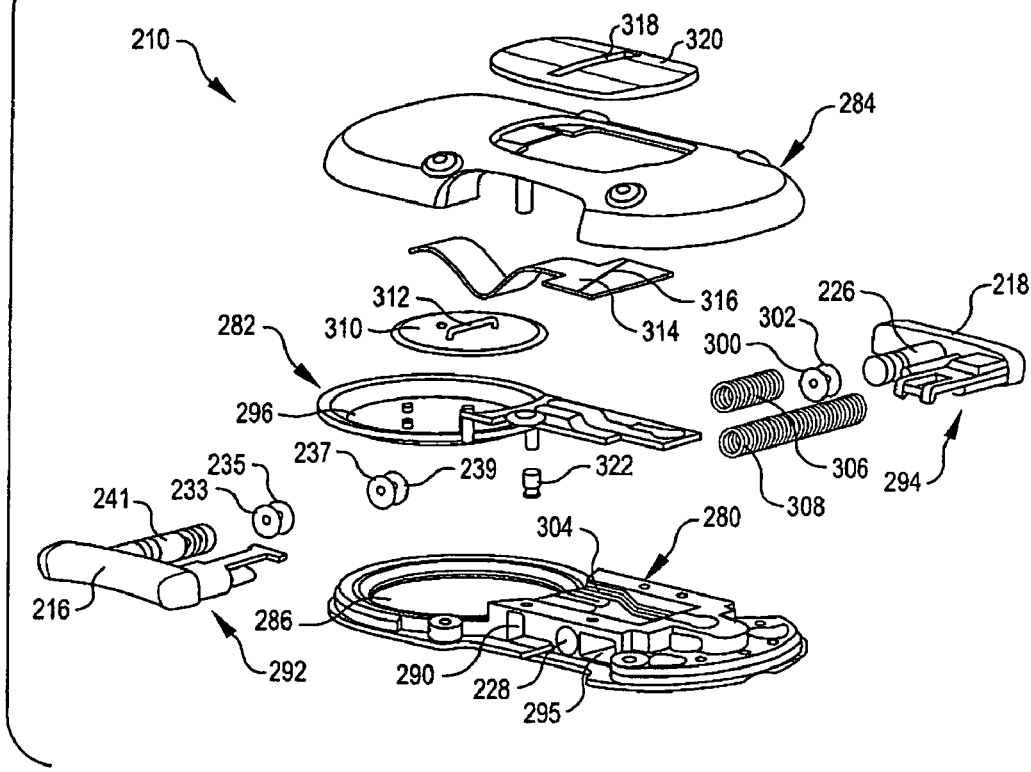
FIG. 12 is an exploded perspective view of the device of FIG. 9.

Referring now to FIG. 12, it is an exploded perspective view of the device of FIG. 9. It shows the various component parts of the device 210. Like the device 10 of FIG. 1, the device 210 is constructed in device layers including a base layer 280, an intermediate layer 282, and the top body layer 284.

Figure 13:
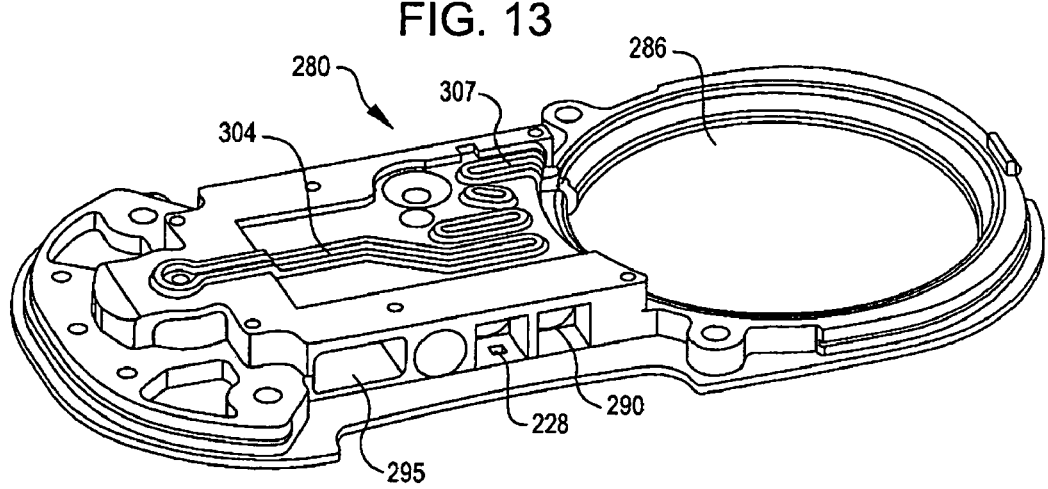
FIG. 13 is a perspective view of one component of the device of FIG. 9.

As may also be seen in FIG. 13, the base layer 280 is a substantially rigid unitary structure that defines a first reservoir portion 286, the pump chamber 228, and a valve chamber 290 for the first and second valves 232 and 234. The base layer 280 may be formed of plastic, for example.

The valve chamber 290 is arranged to receive the valve shuttle bar 241 carried by and extending from the first actuator button 216. O-rings 233, 235, 237, and 239 are arranged to be seated on the shuttle bar 241 to form the first and second valves 232 and 234 respectively (FIG. 10). The actuator button 216 also carries a first portion 292 of the second linkage 254 (FIG. 10). The second linkage is received within a suitably configured bore 295 formed in the base layer 280 and will be described subsequently.

The pump actuator button 218 carries the pump piston 226 and a second portion 294 of the second linkage 254. The pump piston 226 is arranged to be received within the pump chamber 228 and the second portion 294 of the second linkage 254 is arranged to be received within the bore 295 for interacting with the first portion 292. O-rings 300 and 302 are arranged to be seated on the piston 226 to provide a seal against leakage and to prevent external contaminants from entering the piston chamber. The base layer 280 further includes fluid channels 304 that serve to form the fluid conduits illustrated in FIG. 10. Finally, springs 306 and 308 are arranged to spring load the actuator buttons 216 and 218.

The intermediate layer 282 is formed of flexible membrane material. A portion 296 of the intermediate layer is received over the reservoir portion 286 to form the reservoir 222 (FIG. 10). A rigid plate 310 is arranged to be adhered to the portion 296 of the reservoir. Because the layer 282 is flexible membrane, it will move as the reservoir is filled and emptied. The rigid plate 310 will then move with it. The plate includes an eyelet 312 dimensioned to receive an elongated web 314 that forms a part of a medicament level indicator to be described hereinafter. The web 314 carries an indicator line or feature 316.

The top layer 284 is arranged to be received over the intermediate layer 282 and adhered to the base layer. It includes a panel 320 having a view window 318 through which the medicament level indicator line may be observed.

Lastly with respect to FIG. 12, it may be noted the device 210 further includes a pin 322. The pin 322 is a locking pin that is employed to lock the actuator buttons after a last medicament dose is delivered. It also serves to maintain the device fill port, to be described subsequently, in a blocked condition after a last medicament dose is delivered.

Figure 14:
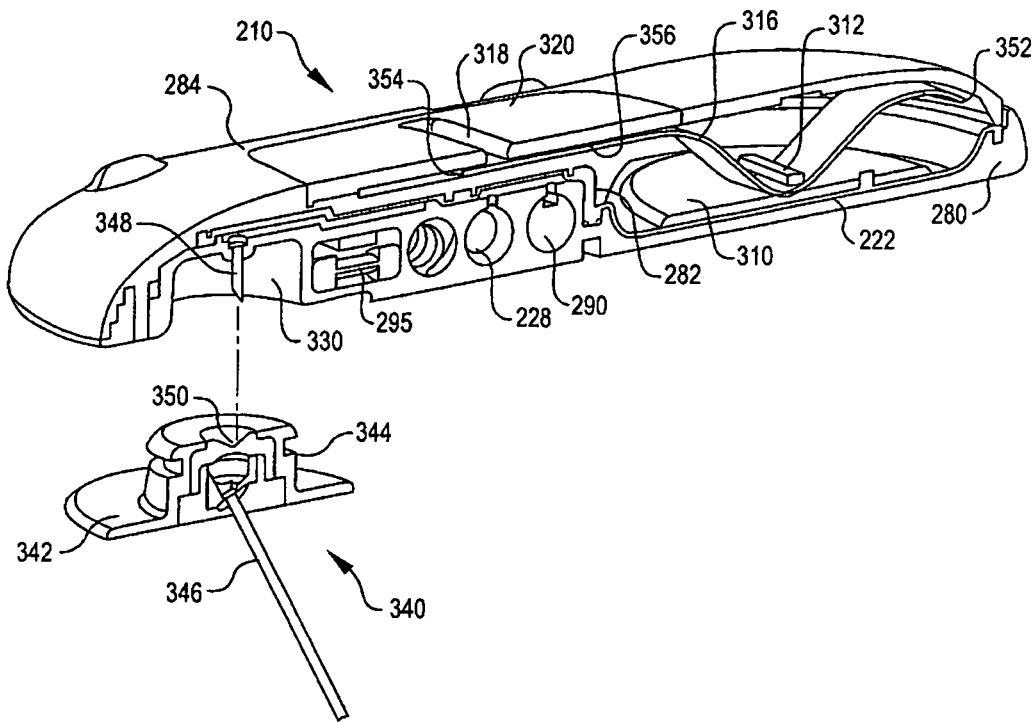
FIG. 14 is a lengthwise sectional view in perspective of the device of FIG. 9 and showing a cannula assembly for use therein in exploded view.
Figure 15:
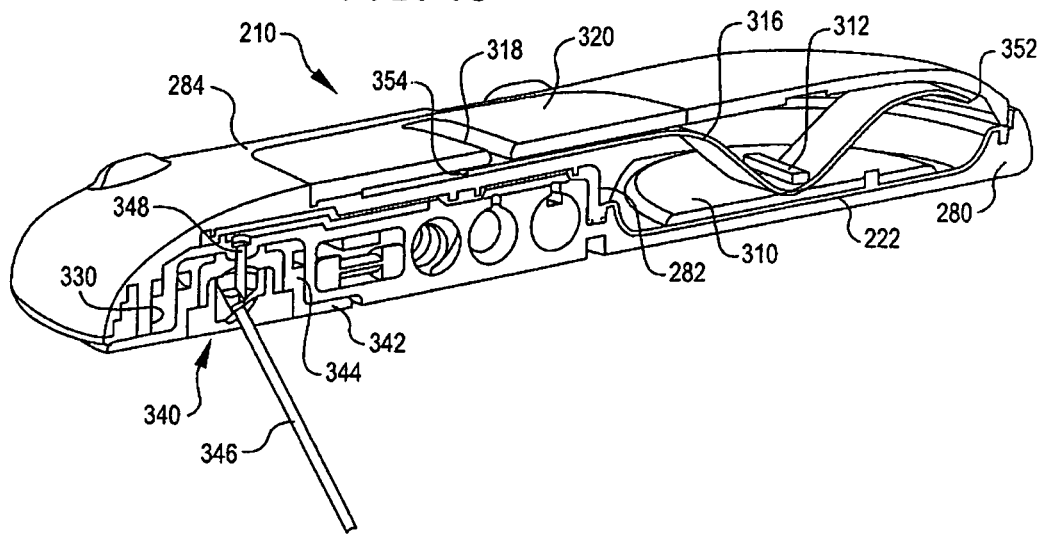
FIG. 15 is a lengthwise sectional view in perspective of the device of FIG. 9 similar to FIG. 14 showing the cannula assembly in operative association with the device.

Referring now to FIGS. 14 and 15, they are lengthwise sectional views, in perspective, of the device of FIG. 9 along with a cannula assembly that may be deployed in the device. FIG. 14 illustrates the previously described layered structure of the device 210 including device layers 280, 282, and 284. As may also be noted in FIG. 14, the device includes a port for receiving a cannula assembly 340. The cannula assembly has a base 342, a generally cylindrical docking structure 344, and a cannula 346. The docking structure 344 is arranged to be received by the port 330 (FIG. 15) after the cannula assembly 340 is applied to the patient's skin with the cannula projecting beneath the patient's skin. The device includes a needle 348 that projects through a septum 350 of the device when the cannula assembly 340 is received by the port 330. This completes the fluid path from the reservoir 222 to the cannula 346. For a more detailed description of such a cannula assembly and the device that utilizes the same, reference may be had to co-pending U.S. application Ser. No. 11/803,007, filed May 11, 2007, and entitled INFUSION ASSEMBLY, which application is owned by the present assignee and incorporated herein by reference.

FIGS. 14 and 15 also clearly illustrate a medicament level indicator embodying the present invention. The rigid plate 310 forms a moveable wall that moves as the medicament volume increases and decreases within the reservoir. The elongated web 316 is preferably formed from a non-elastic, non-compressible, elongated material. It has a first end 352 and a second end 354. The web is fixed at the first end 352 with respect to the rigid plate 310 of the reservoir 222 and is arranged to move in a first plane generally perpendicular to the rigid plate 310 intermediate the first and second ends 352 and 354. Because the web 316 is fixed at the first end 352 and free to move within the eyelet 312, its second end 354 will move in linear movement in a second plane substantially parallel to the rigid member and transverse to the first plane.

As previously mentioned, a panel 320 of the top layer 284 has a window opening 318 to render the medicament level indicia viewable. The cover panel 320 forms a guide channel 356 that receives and confines the web second end to guide the web for linear movement in the second plane substantially transverse to the first plane. As the reservoir is filled or emptied, a glance through the window 318 will provide an indication of the level of the medicament in the reservoir 222.

Figure 16:
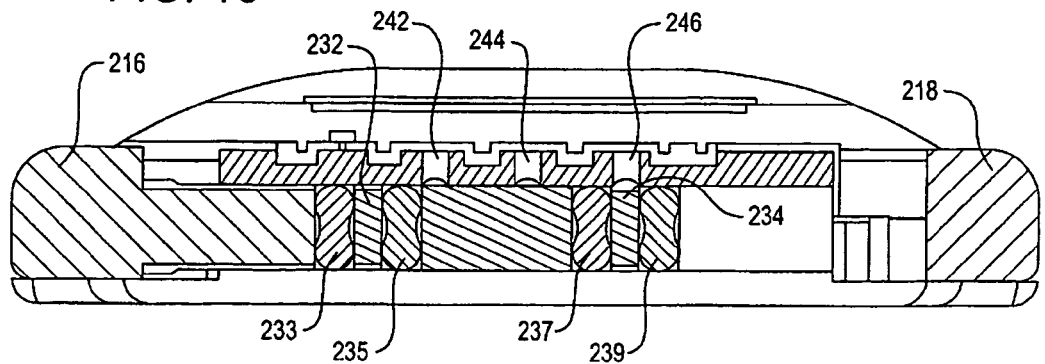
FIG. 16 is a sectional plan view showing the valve configuration of the device of FIG. 9 during pump filling.

Referring now to FIG. 16, it is a sectional plan view showing the valve configuration of the device 210 of FIG. 9 during medicament filling of the pump chamber 228 immediately after a dosage delivery. Here, it may be clearly seen that the first actuator button 216 has an extension comprising the shuttle bar 241 of the valves 232 and 234. Above the valves are the conduits from the reservoir, from the pump, and to the cannula. More particularly, the conduit 242 is in fluid communication with the reservoir 222 (FIG. 10), the conduit 244 is in fluid communication with the pump, and the conduit 246 is in fluid communication with the cannula. The valves are shown with the first valve 232 opened and not blocking the reservoir conduit 242, and the second valve 234 closed and blocking the conduit 246 to the cannula. This permits medicament to flow from the reservoir through conduit 242 and to the pump chamber 228 through conduit 244 as the actuator button 216 returns to its first position. Hence, the pump chamber is filled and ready for the next dosage delivery.

Figure 17:
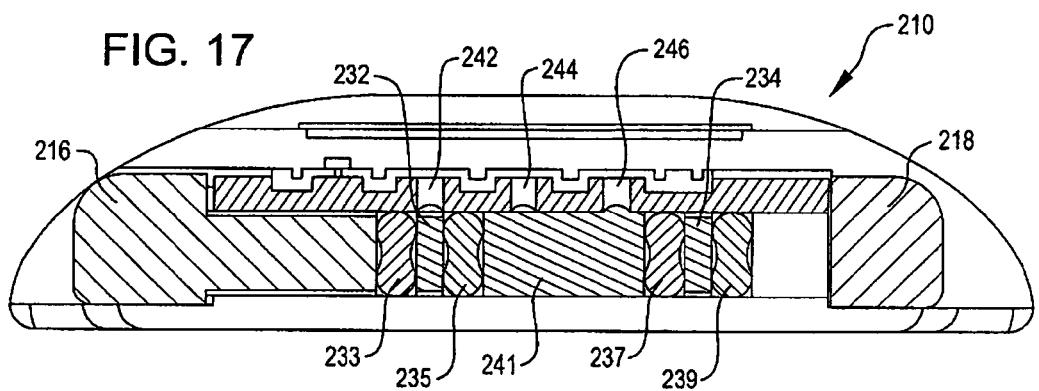
FIG. 17 is a sectional plan view showing the valve configuration of the device of FIG. 9 during medicament delivery.

Referring now to FIG. 17, it is a sectional plan view showing the valve configuration of the device 210 of FIG. 9 during medicament delivery. Here, the valves are shown with the first valve 232 closed and blocking the reservoir conduit 242, and the second valve 234 open permitting medicament to flow from the pump through conduit 244 and to the cannula through conduit 246. As previously mentioned, the first and second valves 232 and 234, respectively, are spaced apart so that conduit 242 is blocked before conduit 246 is opened.

Figure 18:
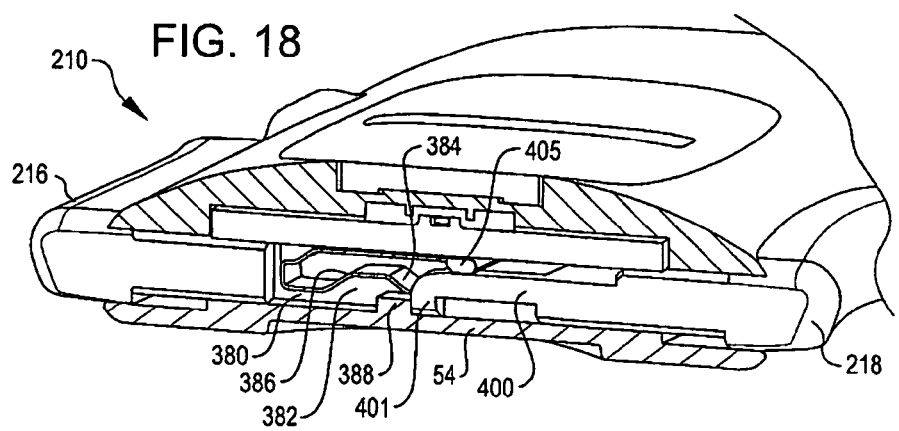
FIG. 18 is a sectional view, in perspective, to an enlarged scale, showing the actuation linkages of the device of FIG. 9 prior to medicament dosage delivery.
Figure 19:
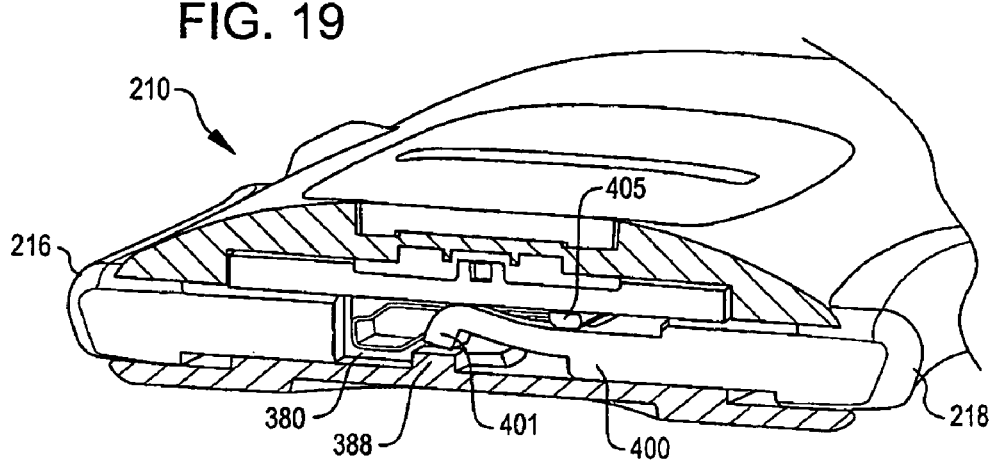
FIG. 19 is a sectional view like that of FIG. 18, showing the actuation linkages of the device of FIG. 9 during medicament dosage delivery.
Figure 20:
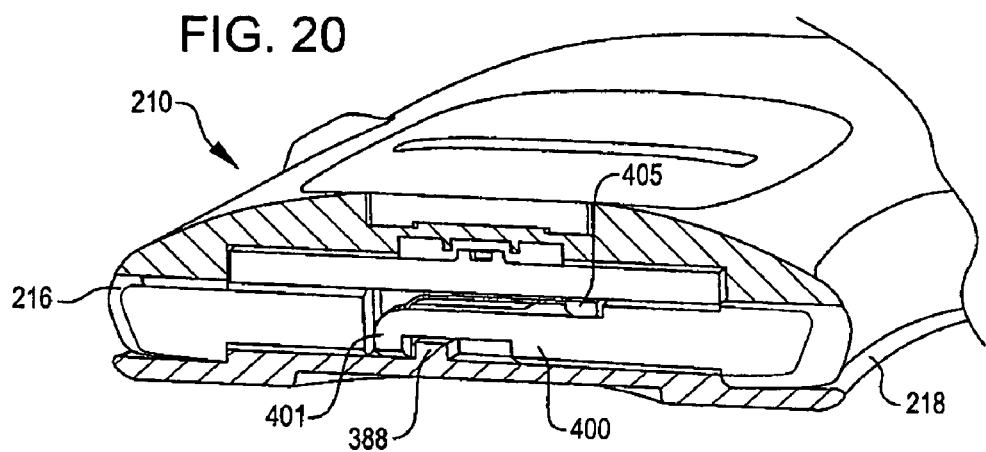
FIG. 20 is a sectional view like that of FIG. 18, showing the actuation linkages of the device of FIG. 9 after medicament dosage delivery.
Figure 21:
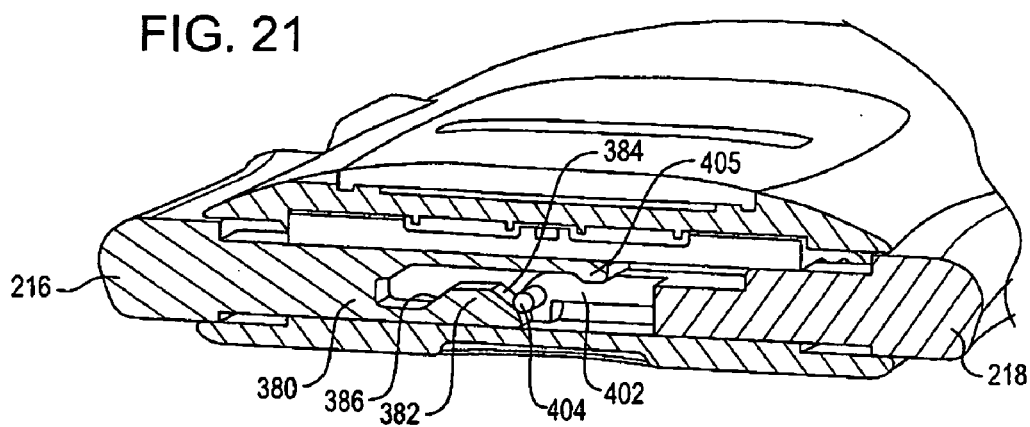
FIG. 21 is a another sectional view, in perspective, to an enlarged scale, showing the operation of the actuation linkages.
Figure 22:
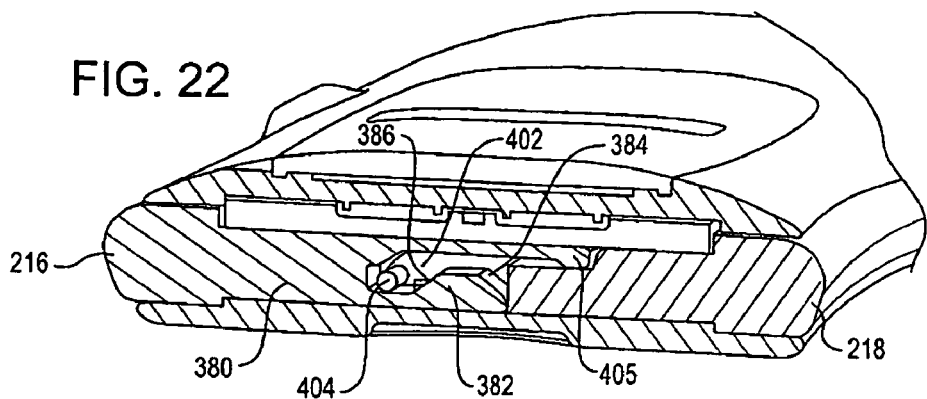
FIG. 22 is another sectional view like that of FIG. 21, in perspective, to an enlarged scale, showing the operation of the actuation linkages.

FIGS. 18-22 show details of the operation of the second linkage 254 of the device 210. Through this discussion, simultaneous reference to more than one drawing figure may be necessary. As may be seen FIG. 18, the first actuator button 216 has an extension 380 that terminates in a block 382 having a first ramp surface 384 and a second ramp surface 386. When the device 210 is actuated, the button 216 is concurrently depressed with pump button 218. It and its extension 380 and bloc 382 are free to move to the right. As seen in FIGS. 18 and 21, the pump actuator button 218 has parallel extensions 400 and 402 which are joined and separated be a rod member 404. As seen in FIG. 18, the extension 400 abuts an abutment 388 which it must clear to be able to move to the left. As shown in FIG. 21, as the button 216 is depressed, its extension 380 moves to the right causing the first ramp surface to engage the rod member 404. Continued movement of the button causes the rod member 404 to rise up under the first ramp surface 384 which in turn causes the extension 400 to begin to move slightly to the left and bend upward about rib 405. Eventually, the rod member 404 rides up the length of the first ramp 384 causing the end 401 of extension 400 to clear the abutment 388 as shown in FIG. 19. The pump button 216 is now able to move freely to the left. When the end 401 of extension 400 totally clears the abutment 388, it will snap behind the abutment 388 as shown in FIG. 20 and become temporarily locked. Meanwhile, as shown in FIG. 22, the rod member 404 has traversed down the second ramp surface 386. The buttons 216 and 218 are now fully depressed.

Hence, from the above, it may be seen that the pump button 218 could not at first move freely while the first actuator button 216 which operates the valves could. As a result, the pump actuation lags behind the valve actuation causing the first valve 232 (FIG. 10) to be closed and the second valve 234 to be opened, establishing a medicament delivery flow path to the cannula, before the pump is able to begin pumping the medicament to the patient. Because this operation occurs quickly, it appears to the patient that both actuator buttons are moving at the same rate.

When the extension 400 of the pump button clears the abutment 388, it becomes locked in a snap action. As in the previous embodiment, this provides positive feedback to the patient that a dosage of medicament was delivered as desired. It also causes a full dose to be delivered. By virtue of the snap action of the pump actuator, only full doses may be administered.

When the medicament has been delivered, the spring loading of the actuator buttons returns the buttons to their first or initial position. During this time, the same timing provided by the block 382 is used for recharging the pump. More specifically, ramp 366 unlatches the end 401 of extension 400 by lifting rod member 404 so that 246 is closed and conduit 242 is opened before the pump is returned by the spring to its initial position. This assures that the pump does not pull medicament from the patient but only from the reservoir. As the piston 226 of the piston pump 224 returns, a full dose of the medicament is drawn up into the piston chamber 228 to ready the device for the next dosage delivery.

Figure 23:
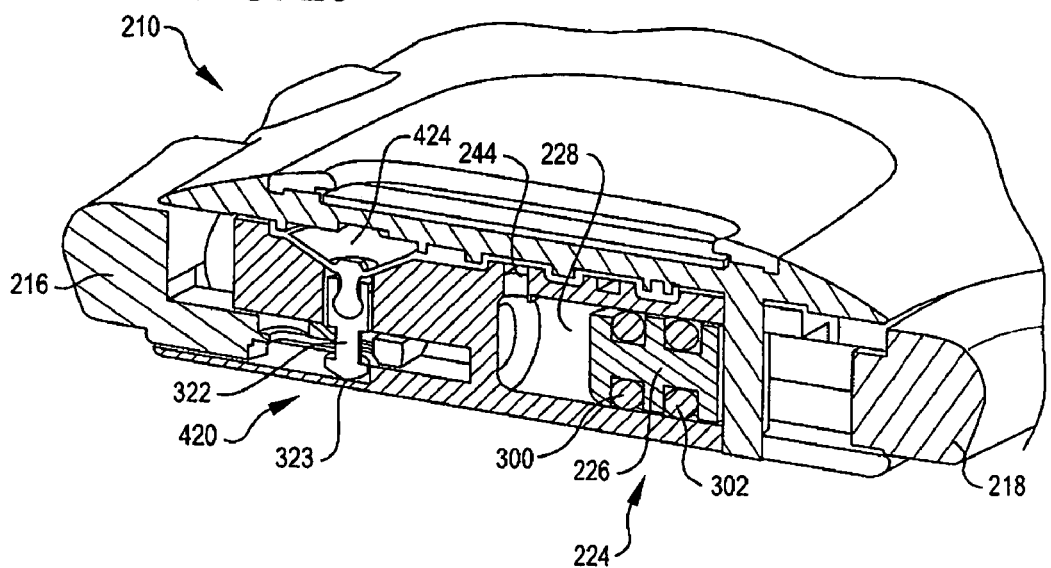
FIG. 23 is still another sectional view showing the last dose lock-out and the device pump during normal medicament delivery actuation.
Figure 24:
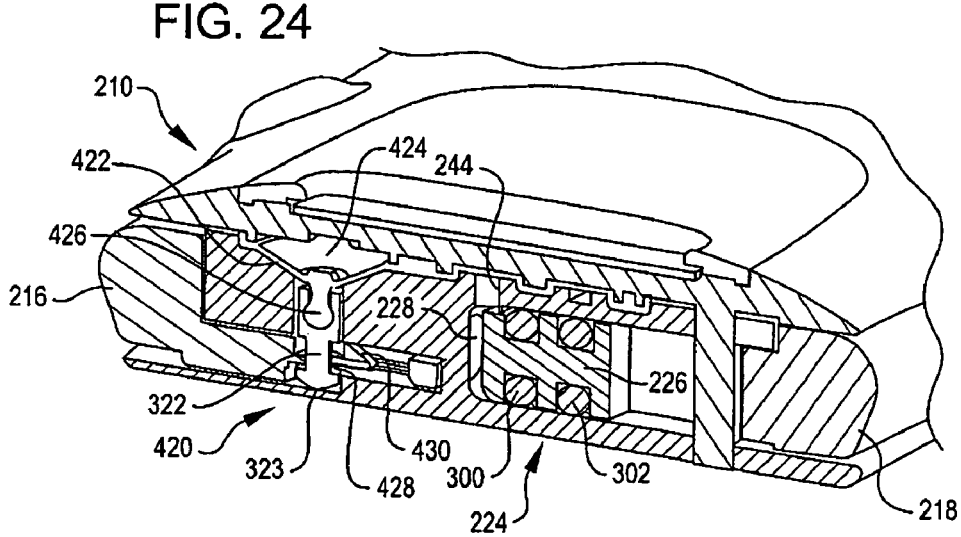
FIG. 24 is a sectional view, like that of FIG. 23, showing the last dose lock-out and device pump after normal medicament delivery.

FIGS. 23 and 24 show the operation of the piston pump 224 in greater detail. Also shown is a last dose lock-out 420 that will be described subsequently. Here it may be seen that the piston 226 of pump 224 is an extension of the pump actuator button 218. Also, it may be seen that the O-rings 300 and 302 seal the piston 226 and the chamber 228. The double O-rings both prevent leakage of medicament from the camber 228 and prevent outside contaminants from entering the chamber 228.

When the pump chamber is filled with medicament as the actuator button is returned from the second position shown in FIG. 24 to the first or initial position shown in FIG. 23 after a dosage delivery, medicament flows from the reservoir, through a conduit 307 (FIG. 13), through a diaphragm chamber 424 and through the conduit 244 to the pump chamber 228. The chamber 424 is defined by a diaphragm 422 formed of flexible membrane material. The diaphragm 422 includes an extension which captures the pin 322, previously shown in the exploded view of FIG. 12. As long as the reservoir has medicament, and hence is not empty, the diaphragm 422 is not affected. In this state, the button 216 is free to be actuated.

As may be noted, the pin is L-shaped at end 323 with an L-extension 428. A capture ramp 430, integral with the actuator button, passes adjacent to the pin 322 and over the L-extension 328. This occurs when the actuator button is depressed as long as the reservoir has sufficient medicament to provide at least one more dosage delivery.

Figure 25:
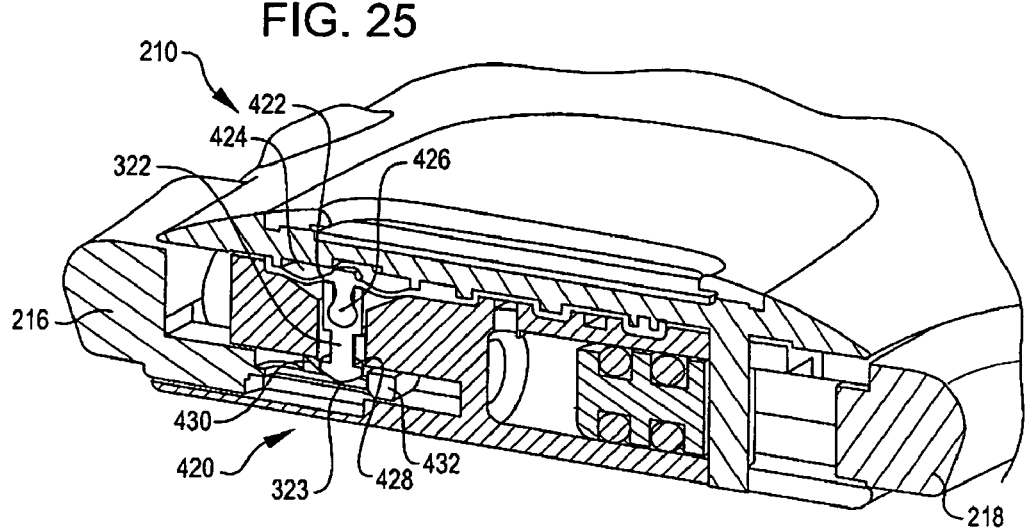
FIG. 25 is a sectional view, like that of FIG. 23, showing the last dose lock-out being conditioned for disabling the actuator upon return of the device pump after a last normal medicament delivery.
Figure 26:
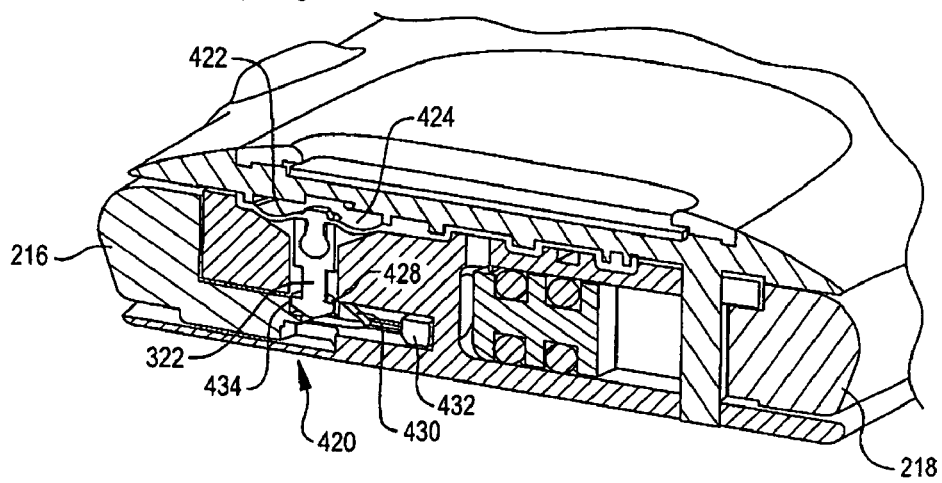
FIG. 26 is a sectional view, like that of FIG. 23, showing the last dose lock-out disabling the actuator upon a final medicament delivery.

Reference may now be had to FIGS. 25 and 26 as the operation of the last dose lock-out 420 is described. When the reservoir has insufficient medicament to support delivery of another dose of medicament, and during the return of the actuator button 218 after what will be the last dose delivered, a negative pressure is created in the diaphragm chamber 424. This causes the diaphragm 422 to be drawn into the chamber 424 due to the absence of liquid medicament in the chamber 424. As the diaphragm 422 is drawn into the chamber 424, the pin 322 is drawn upward with the diaphragm 422 where it engages an abutment 432 connected to the ramp extension 430. The pin 322 is now caused to be captured between the ramp 430 and the abutment 432. The button 216 is now only partially returned to its first position whereas the pump actuator button 218 is free to fully return to its initial position. Upon the next attempted actuation of the device, the L-extension will ride up the ramp 430 and fall into a locked position between the ramp 430 and a shoulder 434 formed in the actuator button 216. The button is now locked and cannot be returned to its first position. The pump actuator button 218 will also be locked in its second position as shown in FIG. 26. This is due to the fact that the first button 216 is not able to return from its second position which, as shown in FIG. 20, causes the end 401 of the extension 400 of the pump actuator 218 be locked between the abutment 388 and actuator button 216. Hence, the device 210 is now locked and cannot be reused.

Figure 27:
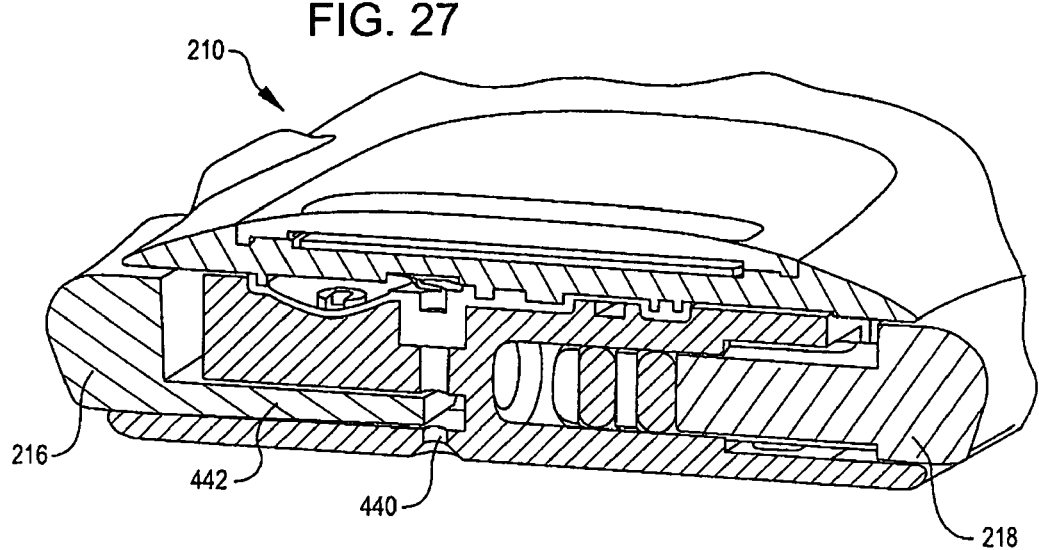
FIG. 27 is another sectional view, to an enlarged scale, showing the device pump and the fill port being blocked during actuation for delivery of medicament.
Figure 28:
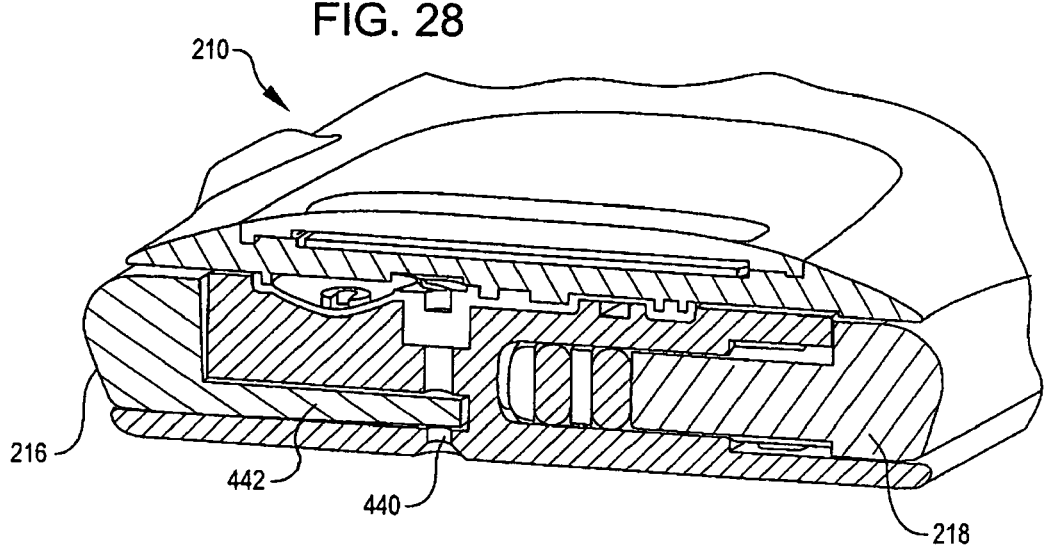
FIG. 28 is another sectional view, like that of FIG. 22, showing the device pump and the fill port being locked in a blocked condition by the last dose lock-out.

Referring now to FIGS. 27 and 28, they illustrate a further aspect of the last dose lock-out. Before the device 210 can be used to deliver a medicament, its reservoir must be filled with a medicament. To this end, the device 210 is provided with a fill port 440 that communicates with the reservoir. When the device 210 is filled with medicament, the actuator buttons 216 and 218 are in their initial positions. The first actuator button 216 further includes another extension 442 which does not cover the fill port 440 when the actuator button 216 is in its initial position. However, when the actuator button 216 is in its fully actuated second position, it does block the fill port 440 as seen in FIG. 28. When the last dose lock-out has the locked the device, the actuator button 216 is left in its fully actuated second position. As a result, the last dose lock-out not only locks both actuator buttons 216 and 218 to disable the device 210, it also blocks the fill port 440 to further render the device disabled.

While particular embodiments of the present invention have been shown and described, modifications may be made. For example, instead of manual actuation and spring loaded return of the valves used herein, constructions are possible which perform in a reversed manner by being spring actuated and manually returned. It is therefore intended in the appended claims to cover all such changes and modifications which fall within the true spirit and scope of the invention as defined by those claims.

What is claimed is:

1. A wearable infusion device comprising:
a reservoir that holds a liquid medicament;
an outlet port that delivers the liquid medicament to a patient;
a pump that displaces a volume of the liquid medicament to the outlet port when actuated, wherein the pump is configured to be actuated multiple times; and
a control that actuates the pump, the control comprising a snap action actuator, wherein the snap action actuator comprises a bendable member, an abutment member that initially engages and holds the bendable member under compression, a first cam surface that, when translated in a first direction, raises the bendable member above the abutment member to release the bendable member, a second cam surface that, when translated in a second direction, opposite the first direction, raises the bendable member above the abutment member and returns the bendable member into engagement with the abutment member under compression, and, a spring that forces the second cam surface to translate in the second direction.

2. A wearable infusion device comprising:
a reservoir that holds a liquid medicament;
an outlet port that delivers the liquid medicament to a patient;
a pump that displaces a volume of the liquid medicament to the outlet port when actuated, wherein the pump is configured to be actuated multiple times; and
a control that actuates the pump, the control comprising a snap action actuator, wherein the snap action actuator comprises a bendable member, an abutment member that initially engages and holds the bendable member under compression, a first cam surface that, when translated in a direction towards the bendable member, raises the bendable member above the abutment member to release the bendable member, a second cam surface that, when translated in a direction away from the bendable member, raises the bendable member above the abutment member and returns the bendable member into engagement with the abutment member under compression, and a spring that forces the second cam surface to translate in the direction away from the bendable member.

3. A wearable infusion device comprising:
a reservoir that holds a liquid medicament;
an outlet port that delivers the liquid medicament to a patient;
a pump that displaces a fixed volume of the liquid medicament to the outlet port when actuated, wherein the pump is configured to be actuated multiple times; and
a control that actuates the pump, the control comprising a displaceable member having a beginning and an end of travel and a snap action actuator that abruptly actuates the pump to displace the fixed volume of liquid medicament upon the displaceable member reaching the end of travel.

4. The device of claim 3, wherein the snap action actuator comprises a bendable member.

5. The device of claim 4, wherein the snap action actuator further comprises an abutment member that initially engages and holds the bendable member under compression.

6. The device of claim 5, wherein the snap action actuator further comprises a first cam surface that, when translated in a first direction, raises the bendable member above the abutment member to release the bendable member.

7. The device of claim 6, wherein the snap action actuator further comprises a second cam surface that, when translated in a second direction, opposite the first direction, raises the bendable member above the abutment member and returns the bendable member into engagement with the abutment member under compression.

8. The device of claim 7, further comprising a spring that forces the second cam surface to translate in the second direction.

9. The device of claim 5, wherein the snap action actuator further comprises a first cam surface that, when translated in a direction towards the bendable member, raises the bendable member above the abutment member to release the bendable member.

10. The device of claim 9, wherein the snap action actuator further comprises a second cam surface that, when translated in a direction away from the bendable member, raises the bendable member above the abutment member and returns the bendable member into engagement with the abutment member under compression.

11. The device of claim 10, further comprising a spring that forces the second cam surface to translate in the direction away from the bendable member.

* * * * *